United States Patent [19]

Wettermann

[11] 4,261,346
[45] Apr. 14, 1981

[54] ENDOSCOPES

[75] Inventor: Ludwig A. Wettermann, Arlington Heights, Ill.

[73] Assignee: Richard Wolf Medical Instruments Corporation, Rosemont, Ill.

[21] Appl. No.: 96,788

[22] Filed: Nov. 23, 1979

[51] Int. Cl.³ .............................................. A61B 1/06
[52] U.S. Cl. .................................................... 128/6
[58] Field of Search .......................... 128/4, 6, 11, 13

[56] References Cited

U.S. PATENT DOCUMENTS

| | | | |
|---|---|---|---|
| 3,677,262 | 7/1972 | Zukowski | 128/6 |
| 3,994,557 | 11/1976 | Hopkins | 128/4 |
| 4,102,333 | 7/1977 | Storz | 128/6 |
| 4,103,680 | 8/1978 | Yoon | 128/6 |

*Primary Examiner*—John D. Yasko
*Attorney, Agent, or Firm*—Kinzer, Plyer, Dorn & McEachran

[57] ABSTRACT

An endoscope having three offset sheaths of which one terminates in the ocular of a telescope lens system included in the instrument, the sheaths being so arranged with the instrument as a whole as to reduce fatigue in the bicep and deltoid muscles of the surgeon.

2 Claims, 3 Drawing Figures

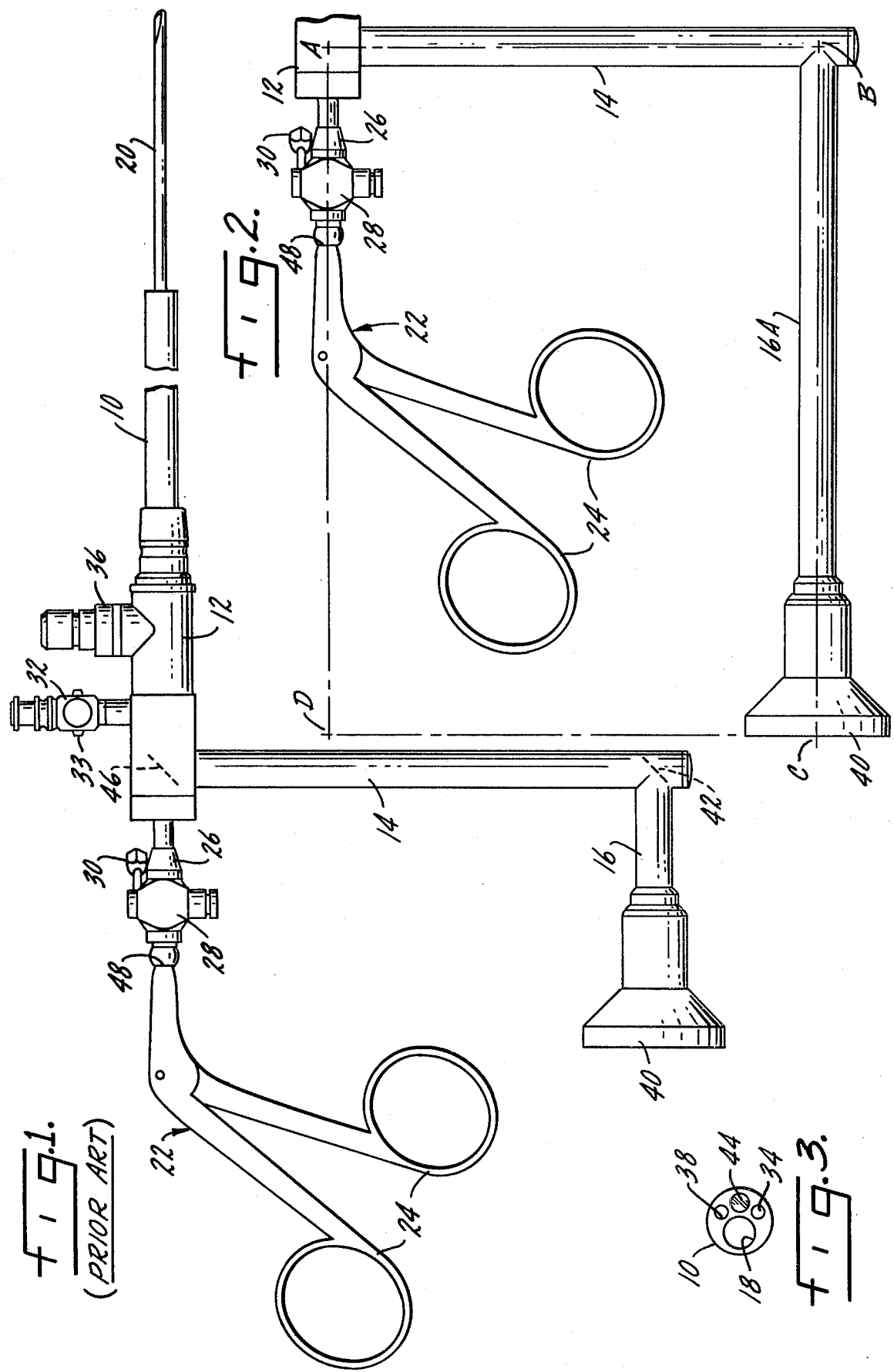

ENDOSCOPES

SUMMARY OF THE INVENTION

This invention relates to a surgical instrument and, in particular, an endoscope.

Endoscopy is particularly tedious in the instance of an arthroscope (knee surgery) and a laparoscope used for abdominal surgery. In the standard instrument, the surgeon observes internal body tissue through an ocular while simultaneously manipulating a forceps or other operating instrument. The surgeon is usually hunched over using one hand to hold the endoscope itself and the other hand to manipulate the operating instrument. For a left-handed surgeon, he will usually steady the endoscope with his right hand as he squints into the ocular and with his left hand will be manipulating the operating instrument.

In the standard instrument, it has been noted muscular fatigue on the part of the surgeon occurs in the biceps (upper arm) and in the deltoid muscle near the shoulder, and it is the primary object of the present invention to reduce muscular fatigue of a surgeon using an endoscope of the foregoing kind. Specifically, it is an object of the present invention to avoid biceps and deltoid muscular fatigue on the part of the surgeon by altering the standard construction so that the arm of the surgeon holding the operating instrument will be extended in a more natural position, rather than being retracted which involves the biceps and deltoid muscles.

BRIEF DESCRIPTION OF THE DRAWINGS

FIG. 1 is a plan view of the known instrument, partly broken away;

FIG. 2 is a fragment of an endoscope showing the present invention but otherwise identical to the known instrument;

FIG. 3 is an end view of the sheath of the instrument shown in FIG. 1.

DETAILED DESCRIPTION OF THE INVENTION

I have found that tedium and muscular fatigue on the part of a surgeon using an endoscope may be considerably reduced, to the advantage of the physician and to the advantage of the patient, by a simple but effective alteration in the dimensions of the known instrument, resulting in the arm of the surgeon being disposed in a more natural or limp position rather than in a position where the biceps and deltoid muscles are tensioned without benefit to the operation which is underway.

FIG. 1 of the drawing is a scaled view of the standard, known instrument which happens to be an arthroscope for knee surgery, but the present invention may be equally embodied in a similar endoscope for abdominal surgery, known as a laparoscope. In any event, the endoscope includes a first, elongated, cylindrical sheath 10 attached to a housing 12. A second elongated sheath 14 is attached to the housing 12 at right angles to the longitudinal axis of the first sheath. A third, short sheath 16 is attached to the second sheath 14 and the longitudinal axis of the sheath 16 is parallel to the longitudinal axis of the first sheath.

The first sheath 10 includes a passage 18 and the housing 12 includes a like, aligned passage (not shown) for receiving the shank or shaft 20 of an operating instrument, here shown as a forceps 22. The distal end (the end remote from the surgeon) of the forceps 22 is the operating end of the instrument and may have different configurations, depending upon the type of operation being performed. In any event, the instrument is manipulated by a pivotal scissors-type grip or handle 24 at the proximal end.

The housing 12 at its proximal end includes a tubular fitting 26 having a passage therethrough (not shown) into which the shank 20 of the operating instrument may be inserted thereby to extend through the housing 12 and the sheath 10 as already noted. The fitting 26 includes a valve housing or chamber 28 and the associated valve (not shown) may be opened or closed by means of a pivoting knob or small handle 30. Thus, by opening the valve in the valve chamber 28 by means of the valve handle 30, the shank of the operating instrument may be inserted through the same, but when the operating instrument is removed, the valve handle will be turned to close the valve, thereby to prevent the escape of body fluids, flushing fluids, or a local anesthesia that may be in use at the time. On the other hand, it will be perceived that when the forceps or other instrument is inserted to occupy the position shown in FIG. 1, the instrument itself closes the valve opening inside valve chamber 28.

Also attached to the housing 12 is a laterally extending fitting 32 equipped with a valve and operating handle 33 by which an anesthesia or flushing fluid may be introduced, flowing through a corresponding passage 34 (FIG. 3) in the sheath 10.

The housing 12 is provided with a second laterally extending fitting 36 to which a fiber optic cable may be attached and the sheath 10 has a passage 38, FIG. 3, to allow light from the fiber optic source to be emitted at the distal end to illuminate the internal body cavity where the operation is being performed.

The surgeon views the internal body tissue through an ocular 40 attached to the proximal end of the third sheath 16. There is a prism 42 at the juncture of the third and second sheath. The instrument includes a telescope lens relay system denoted by reference character 44, FIG. 3, and this lens relay system is aligned with a prism 46 inside housing 12, the two prisms 42 and 46 being aligned as will be evident in FIG. 1. Consequently, the surgeon peering or squinting into the ocular 40 is able to observe the progress of the operation.

Referring to FIG. 1 and assuming the surgeon is left-handed, he will be steadying the endoscope with his right hand while peering into the ocular 40 and he will be holding the operating instrument 22 with his left hand. The operating instrument 22 will have a stop shoulder 48 adjacent the proximal end engaging an opposed stop surface on the fitting 26 so that the surgeon can feel the resistance denoting the operating instrument has been fully inserted.

The instrument of the present invention may be considered identical to the known instrument except for lengthening by a considerable amount the third sheath, denoted by reference character 16A in FIG. 2. By this simple alteration it is found the tedium and fatigue associated with the operation is considerably reduced and this is because by lengthening the third sheath the hand of the physician is so displaced that the bicep and deltoid muscles are in a relaxed state rather than being in a state of tension. This difference in muscular attitude can perhaps be visualized by pointing out that with the right hand of the surgeon gripping the shank of the third sheath 16 of the standard instrument, FIG. 1, and by looking into the ocular 40 with the right eye while holding the forceps handle 24, the hand of the surgeon holding the forceps is near his left ear, which is to say the left arm is crooked considerably and is drawn back with the biceps and deltoid muscles in tension. In comparison, with the shank in 16A held in the right hand and the surgeon peering into the ocular 40 with his right eye, his left hand, holding the forceps 24, is displaced forwardly to be somewhat in front of his face so that both the bicep and deltoid are relaxed and the left arm is not crooked as it is when using the standard, known instrument. Thus, I am not concerned with a mere or arbitrary change in dimension but, rather, I am using a change in dimension to allow muscles to assume a relaxed state compared to a state of tension. Viewed another way, the object of my invention is achieved not by altering the operating technique or designing a rest for the arm of the surgeon but rather by altering the instrument so that the muscles go into a state of relaxation.

In order to define the invention with more clarity, it will be seen, FIG. 2, that the handle of the operating instrument, when fully inserted until the stop 48 is engaged and when considered as rotated into the plane of the drawing sheet, lies substantially within a quadrilateral ABCD defined by extending the axes of the three sheaths until they intersect, together with an axis at the end of the ocular 40 drawn parallel to the axis of the second sheath 14.

In comparison, it can be seen that the handle of the standard operating instrument, FIG. 1, lies outside such a quadrilateral. It is the extension of the third sheath 16A, displacing the ocular 40 beyond the handle of the operating instrument, which results in the handle of the operating instrument being inside the critical quadrilateral.

The embodiments of the invention in which an exclusive property or privilege is claimed are defined as follows:

1. In an endoscope having a housing to which is attached a first elongated sheath having passages therein respectively accommodating a fiber optic light bundle, a lens relay system for a telescope and a surgical operating instrument equipped with a scissors-type handle: a second sheath supported on the housing and extending at right angles to the longitudinal axis of the first sheath; a third sheath attached to the second sheath at right angles to the longitudinal axis thereof and extending parallel to the longitudinal axis of the first sheath; said sheaths containing telescope relay lenses in a common system; the third sheath terminating in a proximal end proximal the surgeon and having a telescope ocular attached thereto; an operating instrument having a shank insertable into the passage assigned thereto in the first sheath and said instrument including a scissors-type handle proximal to the surgeon's hand when so inserted the instrument when so inserted having a stop engageable with a stop on the first sheath thereby to dispose the distal end of the instrument in operating position the lengths of said second and third sheaths being such that when the longitudinal axes of the three sheaths are extended together with an axis extended from the end of the ocular, parallel to the axis of the second sheath, the extended axes intercept to define a quadrilateral within the boundaries of which said handle lies when the handle of the instrument in said operative position is rotated into the plane which is coincident with said quadrilateral.

2. In an endoscope having three sheaths of which a second is joined at right angles to a first, the remaining third being joined at right angles to the second, all sheaths lying in the same plane and the first and third sheaths having parallel longitudinal axes, the sheaths incorporating a telescope lens system terminating in an ocular at the proximal end of the third sheath, the first sheath having a passage for receiving a separate insertable operating instrument having a handle for the surgeon, and said instrument when so inserted having a stop engageable with a stop on the first sheath thereby to dispose the distal end of the instrument in operating position, the improvement characterized by:

the lengths of said second and third sheaths being such that when the longitudinal axes of the three sheaths are extended together with an axis extended from the end of the ocular, parallel to the axis of the second sheath, the extended axes intercept to define a quadrilateral within the boundaries of which said handle lies when the handle of the instrument in said operative position is rotated into the plane which is coincident with said quadrilateral.

* * * * *